United States Patent

Gassen et al.

Patent Number: 5,208,388
Date of Patent: May 4, 1993

[54] 2,2-DIFLUOROCYCLOPROPYL DERIVATIVES

[75] Inventors: Karl-Rudolf Gassen, Odenthal; Bernd Baasner, Leverkusen, both of Fed. Rep. of Germany

[73] Assignee: Bayer Aktiengesellschaft, Leverkusen, Fed. Rep. of Germany

[21] Appl. No.: 763,031

[22] Filed: Sep. 20, 1991

Related U.S. Application Data

[60] Division of Ser. No. 692,825, Apr. 26, 1991, Pat. No. 5,095,147, which is a continuation of Ser. No. 378,545, Jul. 11, 1989, abandoned.

[30] Foreign Application Priority Data

Jul. 19, 1988 [DE] Fed. Rep. of Germany ....... 3824432

[51] Int. Cl.$^5$ ............................................. C07C 35/04
[52] U.S. Cl. ................... 568/700; 568/715; 568/812; 568/41; 568/43; 568/52; 568/55; 568/303; 568/325; 568/420; 568/425; 568/442; 568/647; 562/506; 562/405; 562/432; 562/440; 562/474; 562/491; 562/492; 562/869; 564/161; 564/162; 564/181; 564/190; 564/307; 560/18; 560/35; 560/65; 560/101; 560/102; 560/124
[58] Field of Search ................ 568/700, 715, 812

[56] References Cited

U.S. PATENT DOCUMENTS

| | | | |
|---|---|---|---|
| 3,462,453 | 8/1969 | Popoff et al. | 568/700 |
| 3,856,976 | 12/1974 | Hunter et al. | 560/124 |
| 4,705,788 | 11/1987 | Schriewer et al. | 514/254 |

FOREIGN PATENT DOCUMENTS 135897A 4/1985 European Pat. Off. ............ 568/700

Primary Examiner—Glennon H. Hollrah
Assistant Examiner—Shailendra Kumar
Attorney, Agent, or Firm—Sprung Horn Kramer & Woods

[57] ABSTRACT 2,2-Difluorocyclopropyl derivatives of the formula

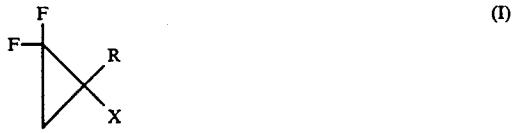
(I)

in which
R represents alkyl, optionally substituted aryl or optionally substituted aralkyl and
X represents hydroxymethyl, 2-hydroxyethyl, isocyanato, amino, amino hydrohalide or a radical of the formula —CO—R$^1$, where
R$^1$ represents hydrogen, hydroxyl, alkoxy, alkyl, halogen or amino,
are intermediates for fungicides.

4 Claims, No Drawings

2,2-DIFLUOROCYCLOPROPYL DERIVATIVES

This is a division of application Ser. No. 692,825, filed Apr. 26, 1991, now U.S. Pat. 5,095,147 which is a continuation of Ser. No. 378,545 filed Jul. 11, 1989, now abandoned.

The present invention relates to novel 2,2-difluorocyclopropyl derivatives, several processes for the preparation thereof, and the use thereof as intermediates for the synthesis of compounds having fungicidal activity.

Certain cyclopropyl derivatives and the use thereof as intermediates for the preparation of azolyl derivatives having fungicidal properties have already been disclosed (cf. EP-OS (European Published Specification) 0,040,345 and EP-OS (European Published Specification) 0,180,136). Thus, 1-(4-chlorophenoxy)-2-cyclopropyl-3-(1,2,4-triazol-1-yl)-propan-2-ol, 1-(4-chlorophenyl)-1-(1-chloro-cycloprop-1-yl)-2-(1,2,4-triazol-1-yl)-ethan-1-ol and 1-(4-chlorophenyl)-1-[1-(2,4-dichlorophenoxy)-cycloprop-1-yl]-2-(1,2, 4-triazol-1-ol can be prepared from corresponding cyclopropyl derivatives and used for combating fungi. The activity of these substances is good, but leaves something to be desired in some cases when low application rates are used.

Novel 2,2-difluorocyclopropyl derivatives of the formula

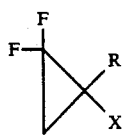

(I)

in which
R represents alkyl, optionally substituted aryl or optionally substituted aralkyl and
X represents hydroxymethyl, 2-hydroxyethyl, isocyanato, amino, amino hydrohalide or the radical of the formula —CO—$R^1$, where
$R^1$ represents hydrogen, hydroxyl, alkoxy, alkyl, halogen or amino,
have now been found.

Furthermore, it has been found that 2,2-difluorocyclopropyl derivatives of the formula (I) can be prepared by a process in which a) vinylcyclopropane derivatives of the formula

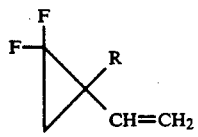

(II)

in which
R has the abovementioned meaning, are reacted either
α) with a strong oxidant in the presence of a diluent, or
β) with ozone in the presence of a diluent and with a reducing agent, or
γ) initially in step 1 with diborane in the presence of a diluent and the resulting product is then reacted in step 2 with a strong oxidant in the presence of a diluent, b) 2,2-difluorocyclopropyl derivatives of the formula

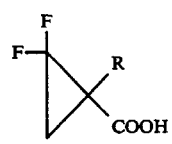

(Ia)

in which
R has the abovementioned meaning, are reacted either
α) with a halogenating agent, if appropriate in the presence of a diluent, or
β) with a complex hydride in the presence of a diluent, or
γ) with organometallic compounds of the formula $R^2$—Li    (III)

in which
$R^2$ represents alkyl, in the presence of a diluent, or c) 2,2-difluorocyclopropyl derivatives of the formula

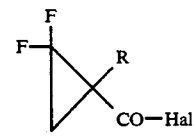

(Ib)

in which
R has the abovementioned meaning and
Hal stands for halogen, are reacted either
α) with an azide group-transferring reagent in the presence of a diluent and the resultant compounds of the formula

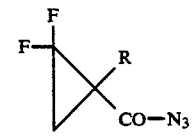

(Ic)

in which
R has the abovementioned meaning, are thermally decomposed in the presence of a diluent, or
β) with alcohols of the formula $R^3$—OH    (IV)

in which
$R^3$ represents alkyl, if appropriate in the presence of a catalyst and if appropriate in the presence of a diluent,
γ) with ammonia, if appropriate in the presence of a diluent, or d) 2,2-difluorocyclopropyl derivatives of the formula

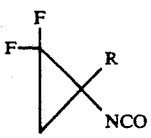

in which
R has the abovementioned meaning, are reacted with hydrohalic acid in the presence of a diluent and if appropriate the resultant compounds of the formula

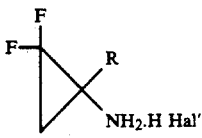

in which
R has the abovementioned meaning and
Hal' represents halogen, are reacted with bases, if appropriate in the presence of a diluent.

Finally, it has been found that the novel 2,2-difluorocyclopropyl derivatives of the formula (I) can be very easily used as intermediates for the preparation of 2,2-difluorocyclopropyl-hydroxyethyl-azoles having fungicidal activity.

Surprisingly, the 2,2-difluorocyclopropyl-hydroxyethyl-azoles which can be prepared from the 2,2-difluorocyclopropyl derivatives of the formula (I) according to the invention show a better fungicidal activity than 1-(4-chlorophenoxy)-2-cyclopropyl-3-(1,2, 4-triazol-1-yl)-propan-2-ol, 1-(4-chlorophenyl)-1-(1-chloro-cycloprop-1-yl)-2-(1,2,4-triazol-1-yl)-ethan-1-ol and 1-(4-chlorophenyl)-1-[1-(2,4-dichlorophenoxy)-cycloprop-1-yl]-2-(1,2, 4-triazol-1-yl)-ethan-1-ol, which are previously known active compounds of similar structure and the same type of action.

Formula (I) provides a general definition of the 2,2-difluorocyclopropyl derivatives according to the invention. Preferred compounds are those in which R represents alkyl having 1 to 4 carbon atoms or phenyl which can be monosubstituted to trisubstituted by identical or different substituents from the series comprising halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, alkoximinomethyl having 1 to 4 carbon atoms in the alkyl moiety and 1 to 4 carbon atoms in the alkoxy moiety, phenoximinoalkyl which has 1 to 4 carbon atoms in the alkyl moiety and which is optionally substituted by alkyl having 1 or 2 carbon atoms and/or halogen, phenyl which is optionally substituted by alkyl having 1 or 2 carbon atoms and/or halogen, and/or phenoxy which is optionally substituted by alkyl having 1 or 2 carbon atoms and/or halogen, or R represents benzyl which can be monosubstituted to trisubstituted in the phenyl moiety by identical or different substituents from the series comprising halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, alkoximinoalkyl having 1 to 4 carbon atoms in the alkyl moiety and 1 to 4 carbon atoms in the alkoxy moiety, phenoximinoalkyl which has 1 to 4 carbon atoms in the alkyl moiety and which is optionally substituted by alkyl having 1 or 2 carbon atoms and/or halogen, phenyl which is optionally substituted by alkyl having 1 or 2 carbon atoms and/or halogen, or phenoxy which is optionally substituted by alkyl having 1 or 2 carbon atoms and/or halogen, and X represents hydroxymethyl, 2-hydroxyethyl, isocyanato, amino, amino hydrochloride, hydrobromide or hydroiodide, or represents the radical of the formula —$COR^1$, where $R^1$ represents hydrogen, hydroxyl, alkoxy having 1 to 6 carbon atoms, alkyl having 1 to 6 carbon atoms, chlorine, bromine, iodine or amino.

Particularly preferred 2,2-difluorocyclopropyl derivatives of the formula (I) are those in which R represents methyl, ethyl, isopropyl, tert.-butyl, or represents phenyl which is optionally monosubstituted or disubstituted by identical or different substituents from the series comprising fluorine, chlorine or methyl, or represents benzyl which can be monosubstituted or disubstituted in the phenyl moiety by identical or different substituents from the series comprising fluorine, chlorine and/or methyl, X represents hydroxymethyl, 2-hydroxymethyl, isocyanato, amino, amino hydrochloride, hydrobromide or hydriodide, or represents the radical of the formula —CO—$R^1$, where $R^1$ represents hydrogen, hydroxyl, alkoxy having 1 to 4 carbon atoms, alkyl having 1 to 4 carbon atoms, chlorine, bromine, iodine or amino.

Very particularly preferred 2,2-difluorocyclopropyl derivatives of the formula (I) are those in which R represents methyl, ethyl, benzyl or phenyl which is optionally monosubstituted or disubstituted by fluorine, chlorine and/or methyl, and X represents hydroxymethyl, 2-hydroxyethyl, isocyanato, amino, amino hydrochloride, hydrobromide or hydroiodide, or represents the radical of the formula —CO—$R^1$, where $R^1$ represents hydrogen, hydroxyl, methoxy, ethoxy, isopropoxy, n-butoxy, methyl, ethyl, isopropyl, n-butyl, chlorine, bromine, iodine or amino.

If, for example, 2,2-difluoro-1-methyl-1-vinylcyclopropane is used as starting substance and potassium permanganate as oxidant, the course of process (a, variant α) according to the invention can be illustrated by the following equation:

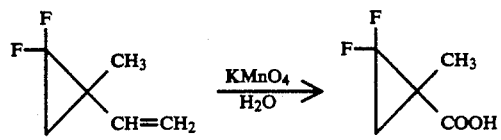

If 2,2-difluoro-1-methyl-1-vinyl-cyclopropane is used as starting substance and ozone as reactant, the course of process (a, variant β) can be illustrated by the following equation:

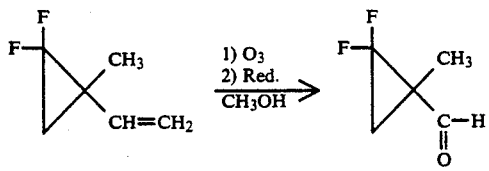

If 2,2-difluoro-1-methyl-1-vinyl-cyclopropane is used as starting substance and diborane and subsequently hydrogen peroxide are used as reactants, the course of process (a, variant γ) according to the invention can be illustrated by the following equation:

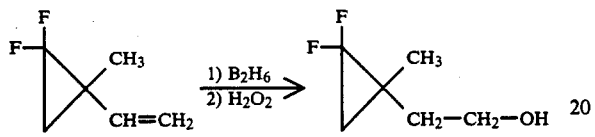

If 2,2-difluoro-1-methyl-1-cyclopropanecarboxylic acid is used as starting substance and thionyl chloride as halogenating agent, the course of process (b, variant α) according to the invention can be illustrated by the following equation:

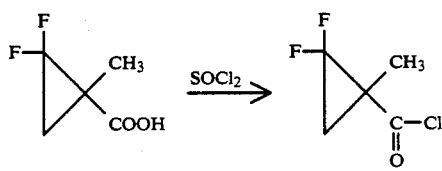

If 2,2-difluoro-1-methyl-1-cyclopropanecarboxylic acid is used as starting substance and lithium aluminum hydride is used as complex hydride, the course of process (b, variant β) according to the invention can be illustrated by the following equation:

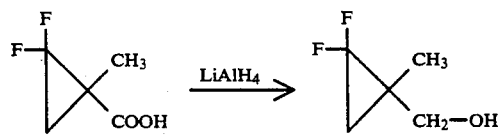

If 2,2-difluoro-1-methyl-cyclopropanecarboxylic acid is used as starting substance and methyllithium as organometallic compound, the course of process (b, variant γ) according to the invention can be illustrated by the following equation:

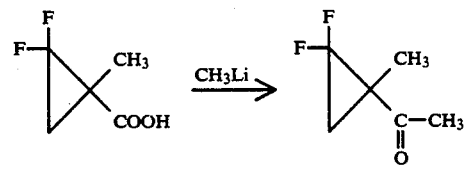

If 2,2-difluoro-1-methyl-1-cyclopropanecarboxylic acid is used as starting substance and trimethylsilyl azide as reactant, the course of process (c, variant α) according to the invention can be illustrated by the following equation:

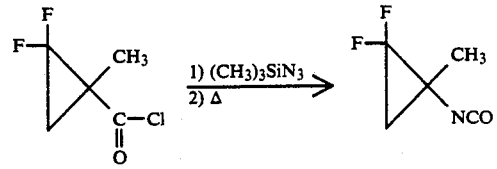

If 2,2-difluoro-1-methyl-cyclopropane-carbonyl chloride is used as starting substance and ethanol as reactant, the course of process (c, variant β) according to the invention can be illustrated by the following equation:

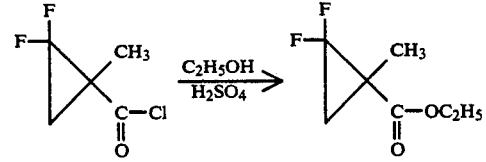

If, 2,2-difluoro-1-methyl-1-cyclopropane-carbonyl chloride is used as starting substance and ammonia as reactant, the course of process (c, variant α) according to the invention can be illustrated by the following equation:

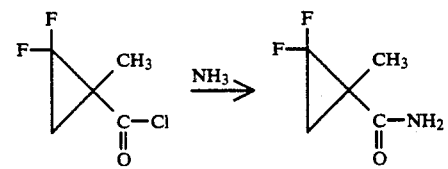

2,2-difluoro-1-methyl-cyclopropyl isocyanate is used as starting substance and concentrated hydrochloric acid as reactant, the course of process (d) according to the invention can be illustrated by the following equation:

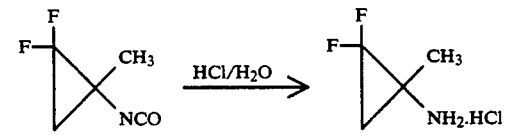

Formula (II) provides a general definition of the vinylcyclopropane derivatives required as starting substances for carrying out process (a) according to the invention. In this formula, R preferably stands for those radicals which have already been mentioned in connection with the description of the substances of the formula (I) according to the invention as being preferred for R.

The vinylcyclopropane derivatives of the formula (II) are known or can be prepared by processes which are known in principle (cf. Liebigs Ann. Chem. 710, 17–35 (1967) and Chem. Ber. 109, 2351–2369 (1976)).

Suitable strong oxidants for carrying out process (a, variant α) according to the invention are all those oxidants which are suitable for splitting olefinic double bonds. Potassium permanganate can preferably be used.

Possible diluents for carrying out variant α of process (a) according to the invention are all solvents which are customary for reactions of this type. Water can preferably be used.

When carrying out process (a, variant α) according to the invention, the temperatures can be varied within a certain range. In general, the process is carried out at temperatures between 0° C. and 60° C., preferably between 10° C. and 50° C.

Process (a, variant α) according to the invention is generally carried out under atmospheric pressure, as are the other processes described in this application. However, it is in each case also possible to carry out the reaction under increased or reduced pressure.

When carrying out process (a, variant α) according to the invention, 2 to 3 moles of strong oxidant are generally employed per mole of vinylcyclopropane derivative of the formula (II). Working up is carried out by customary methods.

Possible reducing agents for carrying out process (a, variant β) according to the invention are all reducing agents which are customary for ozonolyses of this type. Triphenylphosphine, trimethyl phosphite, dimethyl sulphide and hydrogen in the presence of a catalyst can preferably be used.

Suitable diluents for carrying out process (a, variant β) according to the invention are all solvents which are customary for ozonolyses of this type. Alcohols, such as methanol or ethanol, can preferably be used.

When carrying out process (a, variant β) according to the invention, the reaction temperatures can be varied within a certain range. In general, the process is carried out at temperatures between −80° C. and −20° C., preferably between −80° C. and −40° C.

When carrying out process (a, variant β) according to the invention, ozone is passed through the reaction mixture until the reaction is complete. Working up is carried out by customary methods. In general, a procedure is followed in which an excess of reducing agent is added to the reaction mixture and stirring is initially continued with cooling. After the reaction mixture has come to room temperature, it is diluted with water and extracted using an organic solvent which is sparingly soluble in water, and the combined organic phases are dried and distilled.

The diborane required for carrying out process (a, variant γ) according to the invention is generally freshly prepared, for example by reacting boron trifluoride etherate with sodium borohydride in the presence of an inert organic diluent, such as, for example, diglyme. The resultant diborane is directly reacted further.

Possible diluents for carrying out step one of process (a, variant γ) according to the invention are all inert organic solvents which are customary for reactions of this type. Ethers, such as diethyl ether, dioxane or tetrahydrofuran, can preferably be used.

If appropriate, step one of process (a, variant γ) according to the invention is carried out under a protective gas atmosphere, preferably under nitrogen or under argon.

When carrying out process (a, variant γ) according to the invention, the reaction temperatures can be varied within a certain range both in step 1 and in step 2. In general, the reaction is carried out at temperatures between 0° C. and 60° C., preferably between 10° C. and 50° C.

When carrying out step 1 of process (a, variant γ), a stoichiometric amount or, even a subequivalent amount, of diborane is employed per mole of vinylcyclopropane derivative of the formula (II). When the reaction is complete, a procedure is generally followed in which excess vinylcyclopropane derivative of the formula (II) and solvent are removed under reduced pressure. The residue is directly reacted further.

Possible diluents for carrying out step 2 of process (a, variant γ) according to the invention are likewise preferably ethers, such as diethyl ether, tetrahydrofuran and dioxane.

Possible strong oxidants for carrying out step 2 of process (a, variant γ) according to the invention are all customary strong oxidants. Hydrogen peroxide can preferably be used.

When carrying out process (a, variant γ) according to the invention, hydrogen peroxide can be employed in the form of dilute aqueous solutions and in the presence of aqueous alkali hydroxide solution, such as, for example, aqueous sodium hydroxide solution.

When carrying out step 2 of process (a, variant γ) according to the invention, a procedure is generally followed in which the product obtained in step 1 taken up in a solvent and an excess of each aqueous alkali hydroxide solution and aqueous hydrogen peroxide solution or a similar oxidant is added in succession. Working up is generally carried out by extracting the mixture several times using an organic solvent which is sparingly soluble in water, and the combined organic phases are dried and distilled under reduced pressure.

Formula (Ia) provides a general definition of the 2,2-difluorocyclopropyl derivatives required as starting substances for carrying out process (b) according to the invention. In this formula, R preferably has those meanings which have already been mentioned in connection with the description of the substances of the formula (I) according to the invention as being preferred for this radical.

The 2,2-difluorocyclopropyl derivatives of the formula (Ia) can be prepared by process (a, variant α) according to the invention.

Possible halogenating agents for carrying out process (b, variant α) according to the invention are all those substances which are suitable for converting acids to acid halides. Thionyl chloride, sulphuryl chloride, phosphorus trichloride, thionyl bromide and sulphuryl bromide can preferably be used. The acid fluorides and acid iodides can be prepared from the corresponding bromides or chlorides by customary methods.

Suitable diluents for carrying out process (b, variant α) according to the invention are all inert organic solvents which are customary for reactions of this type. Preferably, the particular halogenating agent is simultaneously used as diluent.

When carrying out process (b, variant α) according to the invention, the reaction temperatures can be varied within a relatively wide range. In general, the process is carried out at temperatures between 0° C. and 150° C., preferably between 20° C. and 80° C.

When carrying out process (b, variant α) according to the invention, 1 to 2 equivalents, or alternatively a relatively large excess, of halogenating agent is employed per mole of 2,2-difluorocyclopropyl derivative of the formula (Ia). Working up is carried out by customary methods. In order to prepare acid iodides, acid bromides are reacted with potassium iodide; while acid fluorides are accessible from other acid halides by reaction with fluorides, such as, for example, sodium fluoride, potassium fluoride, caesium fluoride or ammonium fluoride, or by reaction with hydrofluoric acid.

A suitable complex hydride for the preparation of process (b, variant β) according to the invention is preferably lithium aluminum hydride.

Possible diluents for carrying out process (b, variant β) according to the invention are preferably ethers, such as diethyl ether, dioxane or tetrahydrofuran.

When carrying out process (b, variant β) according to the invention, the reaction temperatures can be varied within a relatively wide range. In general, the process is carried out at temperatures between −10° C. and +100° C., preferably between 10° C. and 70° C.

When carrying out process (b, variant β) according to the invention, an excess of complex hydride is generally employed per mole of 2,2-difluorocyclopropyl derivative of the formula (Ia). Working up is carried out by customary methods. In general, a procedure is followed in which mild hydrolysis is carried out by adding water and dilute inorganic acid to the mixture and then extracting using a solvent, and the combined organic phases are dried and distilled.

Formula (III) provides a general definition of the organometallic compounds required as reactants for carrying out process (b, variant γ) according to the invention. In this formula, $R^2$ preferably represents alkyl having 1 to 6 carbon atoms.

The organometallic compounds of the formula (III) are generally known compounds of organic chemistry.

Possible diluents for carrying out process (b, variant γ) according to the invention are all inert organic solvents customary for reactions of this type. Ethers, such as diethyl ether, dioxane or tetrahydrofuran can preferably be used.

When carrying out process (b, variant γ) according to the invention, the reaction temperatures can be varied within a relatively wide range. In general, the process is carried out at temperatures between −100° C. and +50° C., preferably between −78° C. and 0° C.

Process (b, variant γ) is carried out under a protective gas atmosphere, such as, for example, under argon or nitrogen.

When carrying out process (b, variant γ) according to the invention, 1.5 to 3.0 moles, preferably 2.0 moles, of organometallic compound of the formula (III) are generally employed per mole of 2,2-difluorocyclopropyl derivative of the formula (Ia). Working up is carried out by customary methods. In general, a procedure is followed in which the reaction mixture is poured onto ice and inorganic acid, the organic phase is separated off, the aqueous phase is extracted using an organic solvent which is almost immiscible with water, and the combined organic phases are dried and distilled.

Formula (Ib) provides a general definition of the 2,2-difluorocyclopropyl derivatives required as starting substances for carrying out process (c, variant α) according to the invention. In this formula, R preferably has those meanings which have already been mentioned in connection with the description of the substances of the formula (I) according to the invention as being preferred for the radical R. Hal preferably stands for fluorine, chlorine or bromine.

The 2,2-difluorocyclopropyl derivatives of the formula (Ib) can be prepared by process (b, variant α) according to the invention.

Suitable reagents for transferring azide groups when process (c, variant α) according to the invention is carried out are all substances which are customary for reactions of this type. Trimethylsilyl azide can preferably be used.

Possible diluents for carrying out process (c, variant α) according to the invention are all inert organic solvents which are customary for reactions of this type, both for the preparation of the compounds of the formula (Ic) and for their thermal decomposition. Aliphatic or aromatic hydrocarbons, such as hexane, benzene, xylene or toluene can preferably be used.

When carrying out process (c, variant α) according to the invention, the reaction temperatures can be varied within a relatively wide range. In general, the compounds of the formula (Ic) are prepared at temperatures between 0° C. and 30° C., preferably between 5° C. and 25° C. The subsequent thermal decomposition of the compounds of the formula (Ic) is generally carried out between 20° C. and 120° C., preferably between 25° C. and 100° C.

When carrying out process (c, variant α) according to the invention, 1 to 1.5 moles of an azide group-transferring reagent are preferably employed per mole of 2,2difluorocyclopropyl derivative of the formula (Ib). The product of the formula (Ic), which is formed as an intermediate, is thermally decomposed without isolation by slowly increasing the temperature of the reaction mixture. Subsequent working up is carried out by customary methods. In general, a procedure is followed in which the reaction mixture is subjected to fractional distillation.

Formula (IV) provides a general definition of the alcohols required as reactants for carrying out process (c, variant β) according to the invention. In this formula, $R^3$ preferably represents alkyl having 1 to 6 carbon atoms.

The alcohols of the formula (IV) are generally known compounds of organic chemistry.

Possible catalysts for carrying out process (c, variant β) according to the invention are all reaction accelerators which are customary for the preparation of esters from acids or acid halides. Inorganic acids, such as sulphuric acid, and also strong organic acids, such as p-toluenesulphonic acid, can preferably be used. Inorganic bases, such as sodium hydroxide, and also organic bases, such as pyridine or tertiary amines, can likewise be used.

Suitable diluents for carrying out process (c, variant β) according to the invention are all organic solvents which are customary for reactions of this type. Preferably, the alcohol of the formula (IV), employed in excess, also acts as solvent.

When carrying out process (c, variant β) according to the invention, the reaction temperatures can be varied within a relatively wide range. In general, the process is carried out at temperatures between 0° C. and 150° C., preferably between 20° C. and 140° C.

When carrying out process (c, variant β) according to the invention, 1 to 3 moles, or a relatively large excess, of alcohol of the formula (IV), and also a catalytic amount of reaction accelerator are employed per mole of 2,2-difluorocyclopropyl derivative of the formula (Ib). Working up is carried out by customary methods.

Possible diluents for carrying out process (c, variant γ) according to the invention are all inert organic solvents which are customary for reactions of this type. Ethers, such as diethyl ether, dioxane and tetrahydrofuran can preferably be used.

When carrying out process (c, variant γ) according to the invention, the reaction temperatures can also be varied within a relatively wide range. In general, the process is carried out at temperatures between 0° C. and 60° C., preferably between 10° C. and 40° C.

When carrying out process (c, variant γ) according to the invention, 2,2-difluorocyclopropyl derivatives of the formula (Ib) are reacted with an excess of ammonia. Expediently, a procedure is followed in which the 2,2-difluorocyclopropyl derivative of the formula (Ib) is initially introduced as a solution, and gaseous ammonia is passed in to saturation. Working up is carried out by customary methods. In general, a procedure is followed in which the reaction mixture is concentrated under reduced pressure and the product which remains in this process is stirred with water, filtered off with suction and dried.

Formula (Id) provides a general definition of the 2,2-difluorocyclopropyl derivatives required as starting substances for carrying out process (d) according to the invention. In this formula, R preferably has those meanings which have already been mentioned in connection with the description of the substances of the formula (I) according to the invention as being preferred for the radical R.

The 2,2-difluorocyclopropyl derivatives of the formula (Id) can be prepared by process (c, variant α) according to the invention.

Suitable hydrohalic acids for carrying out process (d) according to the invention are preferably hydrochloric acid, hydrobromic acid or hydriodic acid in the form of their aqueous solutions.

Possible diluents for carrying out process (d) according to the invention are all organic solvents which are customary for reactions of this type. Aliphatic or aromatic hydrocarbons, such as hexane, benzene, toluene or xylene can preferably be used.

When carrying out process (d) according to the invention, the reaction temperatures can be varied within a certain range. In general, the process is carried out at temperatures between 0° C. and 150° C., preferably between 10° C. and 100° C.

When carrying out process (d) according to the invention, 1 to 5 moles of hydrohalic acid in the form of an aqueous solution are preferably employed per mole of 2,2-difluorocyclopropyl derivative of the formula (Id). Working up is carried out by customary methods. In general, a procedure is followed in which the reaction mixture is concentrated under reduced pressure and, if appropriate, the residue remaining is purified by customary methods.

If it is intended to prepare the free amines when carrying out process (d) according to the invention, bases are added to the compounds of the formula (Ie), if appropriate in the presence of a diluent. Possible bases for this process preferably are aqueous alkali hydroxide solutions, such as sodium hydroxide solution or potassium hydroxide solution. Suitable solvents are inert organic solvents or water.

When preparing the free amines by process (d) according to the invention, the reaction temperatures can be varied within a relatively wide range. In general, the process is carried out at temperatures between −10° C. and +50° C., preferably between 0° C. and +30° C.

When preparing the free amines by process (d) according to the invention, the compounds of the formula (Ie) are reacted with an excess of base. Working up is carried out by customary methods. In general, a procedure is followed in which the reaction mixture is extracted with an organic solvent which is almost immiscible with water, if appropriate following previous reaction with water, the combined organic phases are dried and concentrated, and the residue remaining is distilled.

The 2,2-difluorocyclopropyl derivatives of the formula (I) according to the invention are suitable as intermediates for the synthesis of plant protection agents, in particular for the preparation of substances having fungicidal activity.

Thus, for example, 2,2-difluorocyclopropylhydroxyethyl-triazoles of the formula

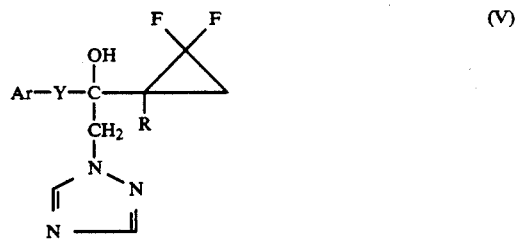

in which
R has the abovementioned meaning,
Ar represents optionally substituted aryl and represents the groups —OCH₂—, —SCH₂—, —CH₂—CH₂— or —CH═CH—, are prepared by a process in which
e) methyl cyclopropyl ketones of the formula

in which
R has the abovementioned meaning, are reacted with chlorinating agents or brominating agents, such as sulphuryl chloride, sulphuryl bromide or bromine, in the presence of a diluent, such as methylene chloride, chloroform or carbon tetrachloride, at temperatures between −10° C. and +60° C., preferably between 0° C. and 40° C., and the resultant halogenoketones of the formula

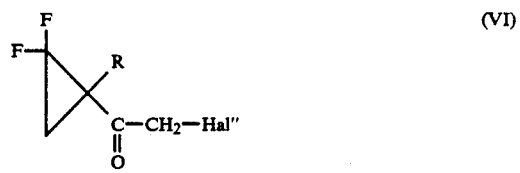

in which
R has the abovementioned meaning and
Hal″ represents chlorine or bromine, are reacted with compounds of the formula

in which
Ar has the abovementioned meaning and
Z represents oxygen or sulphur, in the presence of an acid-binding agent and if appropriate in the presence of a diluent at temperatures between 0° C. and 150° C., preferably between 20° C. and 130° C., and the resultant cyclopropyl ketones of the formula

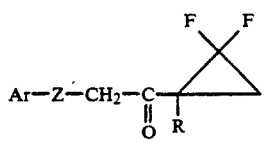 (VIII)

in which
Ar, R and Z have the abovementioned meanings, are reacted either

α) with dimethyloxosulphonium methylide of the formula

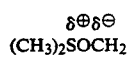 (IX)

or

β) with dimethylsulphonium methylide of the formula

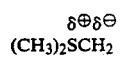 (X)

in the presence of a diluent at temperatures between 0° C. and 100° C., preferably between 10° C. and 60° C., and, finally, the resultant oxiranes of the formula

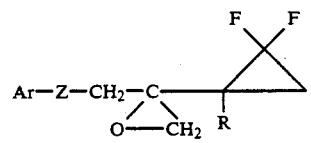 (XI)

in which
Ar, R and Z have the abovementioned meanings, are reacted with 1,2,4-triazole of the formula

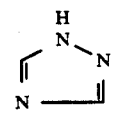 (XII)

in the presence of an acid-binding agent and in the presence of a diluent at temperatures between 0° C. and 200° C., preferably between 50° C. and 150° C., f) methyl cyclopropyl ketones of the formula

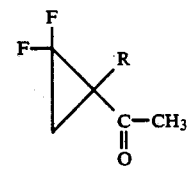 (If)

in which
R has the abovementioned meaning, are reacted with aldehydes of the formula Ar—CHO (XIII)

in which

Ar has the abovementioned meaning, in the presence of a catalyst, such as sodium hydroxide or potassium hydroxide, and also in the presence of a diluent, such as methanol, ethanol, isopropanol, n-butanol or tert.-butanol, at temperatures between 0° C. and 100° C., preferably between 10° C. and 80° C., and, if appropriate, the resultant cyclopropyl ketones of the formula

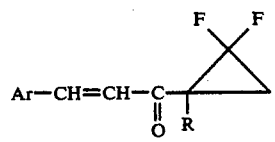 (XIV)

in which
R and Ar have the abovementioned meanings, are hydrogenated with hydrogen in the presence of a hydrogenation catalyst and in the presence of a diluent, and, finally, the cyclopropyl ketones thus obtained, of the formula

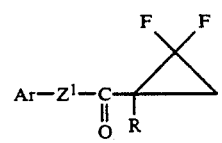 (XV)

Ar and R have the abovementioned meanings and $Z^1$ stands for the groups —CH=CH— or —CH$_2$—CH$_2$—, are reacted α) with dimethyloxosulphonium methylide of the formula

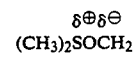 (IX)

or

β) with dimethylsulphonium methylide of the formula

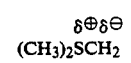 (X)

in the presence of a diluent at temperatures between 0° C. and 100° C., preferably between 10° C. and 60° C., and, finally, the resultant oxiranes of the formula

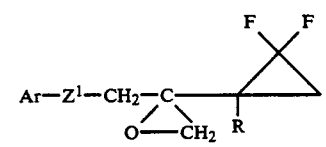 (XVI)

in which
Ar, R and $Z^1$ have the abovementioned meanings, are reacted with 1,2,4-triazole of the formula

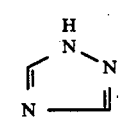 (XII)

in the presence of an acid-binding agent and in the presence of a diluent at temperatures between 0° C. and 200° C., preferably between 50° C. and 150° C.

Furthermore, hydroxyalkinyl-azolyl derivatives of the formula

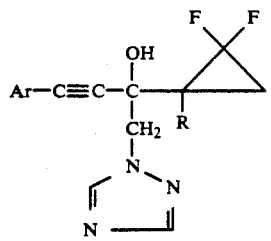

in which Ar and R have the abovementioned meanings, can be prepared by a process in which g) 2,2-difluorocyclopropyl derivatives of the formula

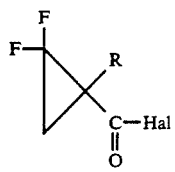

in which

R and Hal have the abovementioned meanings, are reacted with acetyl derivatives of the formula

in which

Ar has the abovementioned meaning, in the presence of a catalyst, such as cooper (I) bromide, and in the presence of an acid-binding agent, such as sodium hydroxide or potassium hydroxide, and in the presence of a diluent, such as toluene, at temperatures between 0° C. and 150° C., preferably between 20° C. and 120° C., and the resultant cyclopropyl ketones of the formula

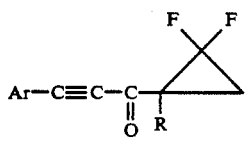

in which

Ar and R have the abovementioned meanings, are reacted with dimethylsulphonium methylide of the formula

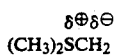

in the presence of a diluent at temperatures between 0° C. and 100° C., preferably between 10° C. and 60° C., and, finally, the resultant oxiranes of the formula

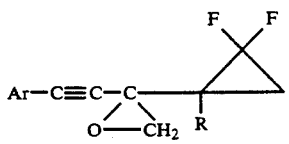

in which

Ar and R have the abovementioned meanings, are reacted with 1,2,4-triazole of the formula

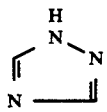

in the presence of an acid-binding agent and in the presence of a diluent at temperatures between 0° C. and 200° C., preferably between 50° C. and 150° C.

The remaining 2,2-difluorocyclopropyl derivatives of the formula (I) can be used in a corresponding manner as intermediates for the synthesis of plant protection agents, in particular of substances having fungicidal activity.

The 2,2-difluorocyclopropyl-hydroxyethyl-triazoles of the formula (V) and the hydroxalkinyl-azolyl derivatives of the formula (XVII) exhibit a powerful microbicidal action and can be employed as fungicides.

Fungicides in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as *Xanthomonas oryzae*; Pseudomonas species, such as *Pseudomonas Lachrymans*; Erwinia species, such as *Erwinia amylovora*; Pythium species, such as *Pythium ultimum*; Phytophthora species, such as *Phytophthora infestans*; Pseudoperonospora species, such as *Pseudoperonospora humuli* or *Pseudoperonospora cubense*; Plasmopara species, such as *Plasmopara viticola*; Peronospora species, such as *Peronospora pisi* or *P. brassicae*; Erysiphe species, such as *Erysiphe graminis*; Sphaerotheca species, such as *Sphaerotheca fuliginea*; Podosphaera species, such as *Podosphaera Leucotricha*; Venturia species, such as *Venturia inaequalis*; Pyrenophora species, such as *Pyrenophora teres* or *P. graminea* (conidia form: Drechslera, syn: Helminthosporium); Cochliobolus species, such as *Cochliobolus sativus* (conidia form: Drechslera, syn: Helminthosporium); Uromyces species, such as *Uromyces appendiculatus*; Puccinia species, such as *Puccinia recondita*; Tilletia species, such as *Tilletia caries*; Ustilago species, such as *Ustilago nuda* or *Ustilago avenae*; Pellicularia species, such as *Pellicularia sasakii*; Pyricularia species, such as *Pyricularia oryzae*; Fusarium species, such as *Fusarium culmorum*; Botrytis species, such as *Botrytis cinerea*; Septoria species, such as *Septoria nodorum*; Leptosphaeria species, such as *Leptosphaeria nodorum*; Cercospora species, such as *Cercospora canescens*; Alternaria species, such as *Alternaria brassicae* and Pseudocercosporella species, such as *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds of the formulae (V) and (XVII) are particularly suitable for combating cereal diseases, such as *Erysiphe graminis, Puccinia recondita, Cochliobolus sativus, Pyrenophora teres, Leptospaeria nodorum* and barley mildew; furthermore rice diseases, such as *Pyricularia oryzae* and *Pellicularia sasakii*; and also *Venturia* species and cucumber mildew. Moreover, the substances have a very good in vitro action.

The active compounds of the formulae (V) and (XVII) can be converted to the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates. As solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

Depending on the manner of application, the application rates of active compounds of the formulae (V) and (XVII) can be varied within a relatively wide range. Thus, in the treatment of parts of plants, the active compound concentrations in the use forms are, in general, between 1 and 0.0001% by weight, preferably between 0.5 and 0.001%. In the treatment of seed, amounts of active compound of 0.001 to 50 g per kilogram of seed, preferably 0.01 to 10 g, are generally required. In the treatment of soil, active compound concentrations of 0.00001 to 0.1% by weight, preferably 0.0001 to 0.02% by weight, are required at the place of action.

The preparation of the 2,2-difluorocyclopropyl derivatives of the formula (I) according to the invention and their use as intermediates for the synthesis of substances having fungicidal activity can be seen from the following examples.

PREPARATION EXAMPLES

Example 1

(I-1)

2.3 kg (14.47 mol) of potassium permanganate are added in portions to 840 g (7.12 mol) of 2,2-difluoro-1-methyl-1-vinyl-cyclopropane in 10 l of water. The mixture is stirred at room temperature for 36 hours, and manganese dioxide is filtered off and rinsed thoroughly with water. The filtrate is acidified using concentrated hydrochloric acid and extracted using dichloromethane. After the organic phase has been dried, the solvent is removed under reduced pressure and the residue is distilled.

In this manner, 750 g (77% of theory) of 2,2-difluoro-1-methylcyclopropanecarboxylic acid of melting point 59°–61° C. are obtained.

Example 2

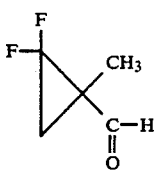
(I-2)

Ozone is passed into a stirred solution of 30 g (0.25 mol) of 2,2-difluoro-1-methyl-1-vinyl-cyclopropane in 250 ml of methanol at -78° C. A solution of 50 g (0.4 mol) of trimethyl phosphite in 50 ml of methanol is then added dropwise, and stirring is continued for one hour at −78° C. The reaction mixture is subsequently warmed slowly to room temperature and then poured into water. The resulting mixture is extracted several times using diethyl ether, and the combined organic phases are dried and distilled under reduced pressure. In this manner, 9.2 g (31% of theory) of 2,2-difluoro-1-methyl-cyclopropane-carboxaldehyde are obtained in form of a liquid of boiling point 110°-112° C./200 torr.

Example 3

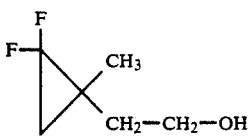
(I-3)

0.23 mol of diborane is produced from 6.7 g (0.18 mol) of sodium borohydride and 33 g (0.23 mol) of boron trifluoride etherate in 130 ml of diglyme, and, with the aid of a stream of nitrogen, is passed into a stirred solution of 30 g (0.25 mol) of 2,2-difluoro-1-methyl-1-vinyl-cyclopropane in 300 ml of dry diethyl ether, at room temperature. The reaction mixture is stirred for one hour more at room temperature and concentrated by stripping off the solvent and the excess alkene under reduced pressure. The residue which remains is taken up in 50 ml of diethyl ether, and 130 ml of 10% strength aqueous sodium hydroxide solution are added. 134 ml of a 30% strength aqueous hydrogen peroxide solution are added dropwise to this mixture at room temperature and with stirring. Stirring is continued for an hour at room temperature, the mixture is extracted several times using diethyl ether, and the combined organic phases are dried and distilled under reduced pressure. In this manner, 13 g (55% of theory) of 2-(2,2-difluoro-1-methyl-cyclopropyl)-ethanol are obtained in form of a liquid of boiling point 65°-67° C./20 torr.

Example 4

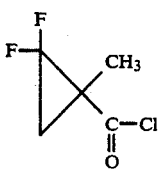
(I-4)

A mixture of 250 g (1.8 mol) of 2,2-difluoro-1-methyl-cyclopropanecarboxylic acid and 700 ml of thionyl chloride is heated slowly and with stirring in a distillation apparatus, with excess thionyl chloride distilling over first and the desired product later. In this manner, 215 g (77% of theory) of 2,2-difluoro-1-methyl-cyclopropane-carbonyl chloride are obtained in form of a liquid of boiling point 121°-122° C.

Example 5

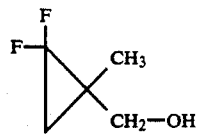
(I-5)

A solution of 50 g (0.35 mol) of 2,2-difluoro-1-methyl-cyclopropane-carboxylic acid in 50 ml of diethyl ether is added dropwise at room temperature to a stirred suspension of 25 g (0.66 mol) of lithium aluminum hydride in 250 ml of dry diethyl ether. The mixture is subsequently refluxed for 4 hours, then allowed to cool to room temperature and carefully hydrolyzed by slowly adding water and concentrated hydrochloric acid. The resultant mixture is extracted several times using diethyl ether, and the combined organic phases are dried and distilled through a Vigreux column. In this manner, 34.5 g (77% of theory) of 2,2-difluoro-1-methyl-cyclopropyl-methanol are obtained in form of a liquid of boiling point 136°-139° C.

Example 6

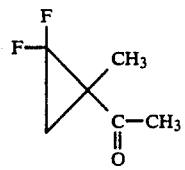
(I-6)

333 ml of a 1.5-molar methyllithium solution (0.5 mol) are added dropwise at −78° C. under nitrogen to 34 g (0.25 mol) of 2,2-difluoro-1-methylcyclopropanecarboxylic acid in 250 ml of dry diethyl ether, with stirring. Stirring is continued for one hour at −78° C., and the reaction solution is then warmed to 0° C. and poured onto 500 g of ice and 50 ml of concentrated hydrochloric acid. The organic phase is separated off, and the aqueous phase is extracted using ether. The combined organic phases are dried over sodium sulphate, the solvent is distilled off, and the product is distilled under slightly reduced pressure.

21 g (63% of theory) of 2,2-difluoro-1-methylcyclopropyl methyl ketone of boiling point 58°-60° C./60 mbar are obtained.

Example 7

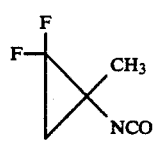
(I-7)

30.9 g (0.2 mol) of 2,2-difluoro-1-methyl-cyclopropane-carbonyl chloride are added dropwise in the course of 10 minutes at 20° C. to a stirred solution of 28 g (0.24 mol) of trimethylsilyl azide in 120 ml of toluene. The temperature of the stirred reaction mixture is subsequently increased to 90° C. in the course of 3 hours.

Stirring is continued until the evolution of gas has ceased. The course of the reaction is monitored by IR spectroscopy by occasionally determining the decrease of the azide band at 2130 cm$^{-1}$, by taking samples. When the reaction is complete, distillation is carried out. In this manner, 12.5 g (47% of theory) of 2,2-difluoro-1-methyl-cyclopropyl isocyanate are obtained in form of a liquid of boiling point 95°–97° C.

Example 8

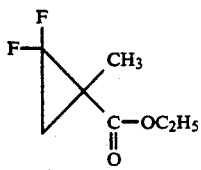
(I-8)

35 ml of ethanol are added dropwise at 20° C. to 15.45 g (0.1 mol) of 2,2-difluoro-1-methyl-cyclopropanecarbonyl chloride, with stirring. After the addition of 2 drops of concentrated sulphuric acid, the reaction mixture is refluxed for another hour. Excess ethanol is subsequently distilled off, and the residue is dried and distilled under atmospheric pressure. In this manner, 14.2 g (87% of theory) of ethyl 2,2-difluoro-1-methylcyclopropane-carboxylate are obtained in form of a liquid of boiling point 141°–143° C.

Example 9

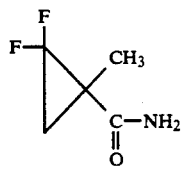
(I-9)

Gaseous ammonia is passed for 90 minutes into a stirred solution of 15.45 g (0.1 mol) of 2,2-difluoro-1-methyl-cyclopropane-carbonyl chloride in 80 ml of dioxane at 20° to 30° C. The resultant suspension is then evaporated to dryness under a water pump vacuum. The residue remaining is stirred with 50 ml of water, filtered off with suction and dried. In this manner, 11 g (81% of theory) of 2,2-difluoro-1-methyl-cyclopropyl-carboxamide in form of a solid substance of melting point 125°–127° C. are obtained.

Example 10

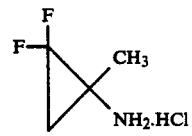
(I-10)

50 ml of concentrated hydrochloric acid are added to a solution of 13 g (0.1 mol) of 2,2-difluoro-1-methylcyclopropyl isocyanate in 100 ml of toluene, and the mixture is stirred at room temperature for 16 hours. The reaction mixture is subsequently heated at 50° C. for another hour, and the solvent is then stripped off completely under reduced pressure. 9 g (63% of theory) of 2,2-difluoro-1-methyl-cyclopropylamine hydrochloride remain, in form of a solid substance of melting point 140°–142° C. (decomposition).

Example 11

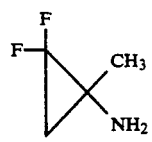
(I-11)

12 g (0.06 mol) of 20% strength aqueous sodium hydroxide solution are added dropwise at 0° to 5° C. to a stirred mixture of 7.2 g (0.05 mol) of 2,2-difluoro-1-methyl-cyclopropylamine hydrochloride and 20 ml of water. The reaction mixture is extracted twice using diethyl ether, and the combined organic phases are dried over magnesium sulphate and concentrated under reduced pressure. The residue remaining is distilled off under reduced pressure. In this manner, 3.9 g (73% of theory) of 2,2-difluoro-1-methylcyclopropylamine are obtained in form of a liquid of boiling point 25°–30° C./15 mbar. Preparation of compounds of the formulae (V) or (XVII):

Example 12

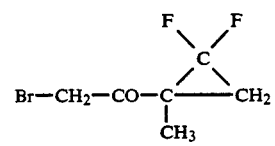
(VI-1)

A solution of 4.7 ml (0.09 mol) of bromine in 30 ml of methylene chloride is added dropwise to a stirred solution of 12.5 g (0.09 mol) of 1-acetyl-1-methyl-2,2-difluoro-cyclopropane in 50 ml of methanol. When decoloration is complete, the reaction mixture is poured into 200 ml of water, and the mixture is extracted using methylene chloride. After concentration under reduced pressure, 20 g (GC content 47%; 47% of theory) of crude 1-bromoacetyl-1-methyl-2,2-difluorocyclopropane, which is reacted directly without further purification, are obtained.

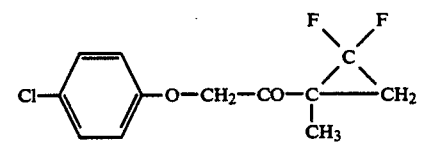
(VIII-1)

6 g (0.028 mol) of 1-bromoacetyl-1-methyl-2,2difluorocyclopropane are refluxed for 16 hours and with stirring in 30 ml of acetone with the addition of 4.4 g (0.032 mol) of potassium carbonate and 4.1 g (0.032 mol) of 4-chlorophenol. The mixture is diluted with water, the product is extracted using methylene chloride, and the organic phase is washed once with dilute sodium hydroxide solution and then with water, and then concentrated under reduced pressure.

6 g 1-(4-chlorophenoxyacetyl)-1-methyl-2,2-difluorocyclopropane are obtained as a crude product with a content (GC) of 66% (54.4% of theory).

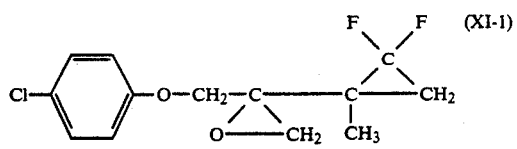

2.4 g (0.044 mol) of sodium methoxide are added to a solution of 30 ml (0.04 mol) of a 1.36-molar solution of trimethylsulphonium methyl sulphate in acetonitrile, and the mixture is stirred for 30 minutes at room temperature. 5.8 g (0.022 mol) of 1-(4-chlorophenoxyacetyl)-1-methyl-2,2-difluorocyclopropane are then added, and the mixture is stirred for 16 hours at 20° C. The reaction mixture is poured into 200 ml of water, the mixture is extracted using methylene chloride, and the organic phase is washed with water and concentrated.

4.3 g (GC purity of 73%; 71.6% of theory) of 2(4-chlorophenoxymethyl)-2-(2, 2-difluoro-1-methylcyclopropyl)-oxirane are obtained as a viscous resin which is reacted further directly.

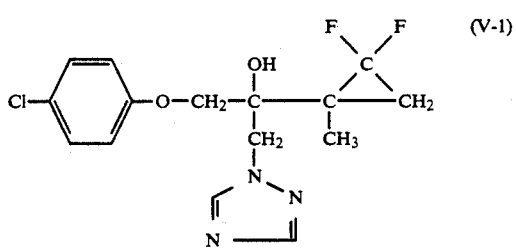

4.2 g (0.015 mol) of 2-(4-chlorophenoxymethyl)-2(2,2-difluoro-1-methylcyclopropyl)-oxirane, 2.1 g (0.03 mol) of 1,2,4-triazole and 4.2 g (0.03 mol) of potassium carbonate are stirred in 30 ml of dimethylformamide for 6 hours at 90° C.

After the solvent has been removed on an oil pump, the residue is stirred with water/methylene chloride, and the organic phase is separated off and concentrated. The residue is purified by means of column chromatography (chloroform/ethyl acetate =4:1) on silica gel.

2.3 g (44.6% of theory) of 1-(4-chlorophenoxy)-2-(2, 2-difluoro-1-methylcyclopropyl)-2-hydroxy-3-(1,2,4-triazol-1-yl)-propane of melting point 110° C. are obtained.

Example 13

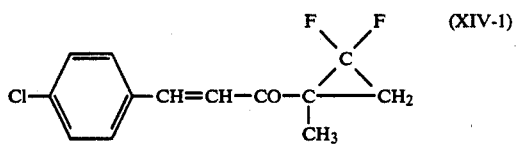

A solution of 15.5 g (0.11 mol) of p-chlorobenzaldehyde in 20 ml of methanol is added at 20° C. and with stirring to 15 g (0.11 mol) of 1-acetyl-2,2-difluoro-1-methylcyclopropane in 20 ml of 10% strength methanolic sodium hydroxide solution. After 15 minutes, 40 ml more of 10% strength methanolic sodium hydroxide solution are added, and the mixture is stirred for 16 hours more at room temperature. The reaction mixture is poured into water, the mixture is extracted using methylene chloride, and the organic phase is washed with water and concentrated under reduced pressure.

25 g (88% of theory) of crude 2,2-difluoro-1-methylcyclopropyl 2-(4-chloropenyl)-ethen-1-yl ketone are obtained as an oil which can be reacted further directly.

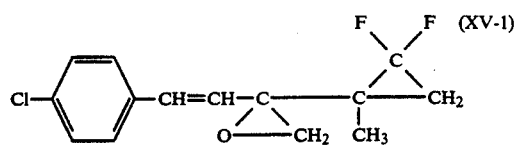

3.6 g (0.066 mol) of sodium methoxide are added to 41 ml (0.06 mol) of a 1.46-molar solution of trimethylsulphonium methyl sulphate in acetonitrile, and the mixture is stirred for 30 minutes at room temperature. A solution of 10 g (0.039 mol) of (2,2-difluoro-1-methylcyclopropyl)-[2-(4-chlorophenyl)-ethen-1-yl] ketone in 100 ml of acetonitrile is subsequently added, and the mixture is stirred for 16 hours at room temperature. The reaction mixture is then poured into water and extracted with methylene chloride, and the organic phase is washed twice with water and concentrated under reduced pressure.

6.8 g (GC purity 38%; 24% of theory) of 2-(2,2-difluoro-1-methylcyclopropyl)-2-[2-(4-chlorophenyl)-ethen-1-yl]-oxirane, which is reacted directly without further purification, are obtained.

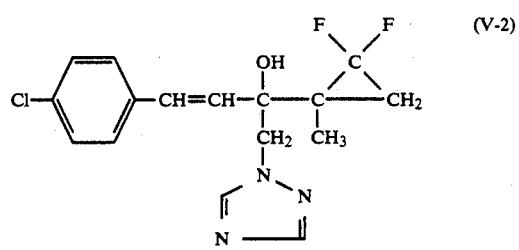

1.4 g (0.048 mol) of 80% strength sodium hydride are added in portions to a solution of 3.3 g (0.048 mol) of 1,2,4-triazole in 30 ml of dimethylformamide, and the mixture is stirred for 30 minutes at 20°-30° C. 6.6 g (0.024 mol) of 2-(2,2-difluoro-1-methyl-cyclopropyl)-2-[2-(4-chlorophenyl)-ethen-1-yl ]-oxirane are subsequently added, and the mixture is stirred for 16 hours at 90° C. The reaction mixture is then poured into water, the mixture is extracted using methylene chloride, the organic phase is concentrated under reduced pressure and the residue is purified by chromatography on silica gel (chloroform/ethyl acetate=4:1).

2.4 g (29.6% of theory) of 1-(4-chlorophenyl)-3-(2, 2-difluoro-1-methylcyclopropyl)-3-hydroxy-4-(1,2,4-triazol-1-yl)-but-1-ene of melting point 131° C. are obtained.

The substances of the formula (V) listed in the table below are also obtained following the methods indicated in Examples 12 and 13 and following the processes disclosed in the description.

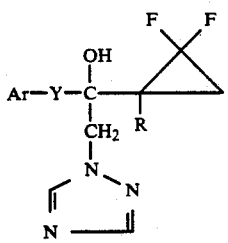

(V)

| Example No. | Compound No. | Ar | Y | R | Physical constant m.p.(°C.) |
|---|---|---|---|---|---|
| 14 | V-3 | F₃CO—⌬— | —OCH₂— | CH₃ | resin |
| 15 | V-4 | Cl—⌬(Cl)— | —OCH₂— | CH₃ | resin |
| 16 | V-5 | Cl—⌬— | —CH₂CH₂— | CH₃ | 112 |
| 17 | V-6 | F—⌬(F)— | —OCH₂— | CH₃ | resin |
| 18 | V-7 | ⌬(F)— | —OCH₂— | CH₃ | resin |
| 19 | V-8 | Cl—⌬(CH₃)— | —OCH₂— | CH₃ | resin |

Example 20

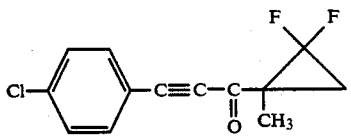
(XIX-1)

3.7 g (0.1 mol) of p-chlorophenyl-acetylene are added to a mixture of 10.1 g (0.1 mol) of triethylamine, 1.4 g (0.01 mol) of copper(I) bromide and 55 ml of toluene, and the mixture is stirred for 30 minutes at room temperature under argon. After the reaction mixture has been heated to 55° C., 15.5 g (0.1 mol) of 1-methyl-2,2-difluoro-cyclopropanecarbonyl chloride are added dropwise. After this, the mixture is stirred for 8 hours at 90° C., and then cooled and filtered. The filtrate is washed in succession with dilute aqueous hydrochloric acid and water and concentrated under reduced pressure. 19.2 g of a dark oil remain, which is distilled using a bulb tube. At 0.1 mbar and a jacket temperature of 120° C., a yellow oil passes over which solidifies on standing. 8.4 g (33% of theory) of 2-(4-chlorophenyl)-ethin-1-yl 2,2-difluoro-1-methylcycloprop-1-yl ketone of melting point 67°-68° C. are obtained.

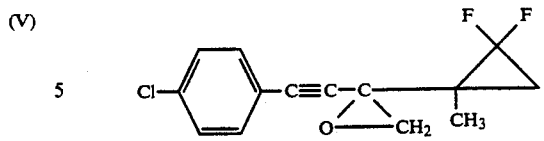

A mixture of 13 g of dimethyl sulphide and 4.8 g of dimethyl sulphate is initially stirred for 2 hours at room temperature, and 18 ml of tert.-butanol and 8.9 g of 2-(4-chlorophenyl)-ethin-1-yl 2,2-difluoro-1-methylcycloprop-1-yl ketone are then added. The mixture is stirred for 30 minutes at room temperature and cooled to 10° C., and a solution of 4.5 g of potassium tert.-butoxide in 32 ml of tert.-butanol is then added in the course of one hour, with stirring. Stirring of the reaction mixture is continued for 3 hours at 10° C., and the mixture is then concentrated by stripping off the diluent under reduced pressure. The residue is taken up in methylene chloride, washed three times with water and dried, and is reconcentrated under reduced pressure. 6.4 g (68% of theory) of 2-[2-(4-chlorophenyl)-ethin-1-yl]-2-(2,2-difluoro-1- 1-methyl-cyclo-prop-1-yl)-oxirane remain in the form of an oil which is reacted further without additional purification.

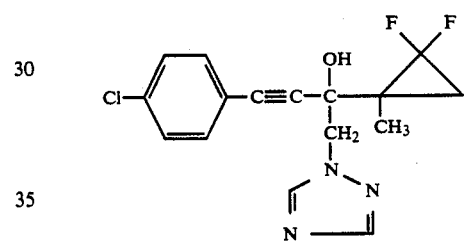

3,5 g of 2-[2-(4-chlorophenyl)-ethin-1-yl]-2-(2, 2-difluoro-1-methyl-cycloprop-1-yl)-oxirane are added to a stirred mixture of 0.9 g (0.013 mol) of 1,2,4-triazole, 1.8 g (0.013 mol) of ground potassium carbonate and 30 ml of acetonitrile at room temperature. The mixture is refluxed for 8 hours, then cooled, diluted with water and extracted three times using methylene chloride. The combined organic phases are washed with water, then dried and concentrated under reduced pressure. In this manner, 3.8 g of a dark oil are obtained which is purified by column chromatography (petroleum ether-/ethyl acetate=1) on silica gel. 2.1 g (48% of theory) of 1-(4-chlorophenyl)-3-(2, 2-difluoro-1-methyl-cycloprop-1-yl)-4-(1,2,4-triazol-1-yl)-but-1-in-3-ol remain in the form of 5 a solid substance of melting point 113°-115° C. In the following Use Examples, the compounds of the formulae indicated below were employed as comparison substances:

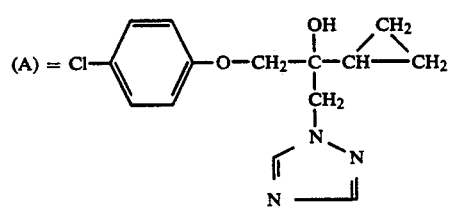

(disclosed in EP-OS (European Published Specification) 0,040,345)

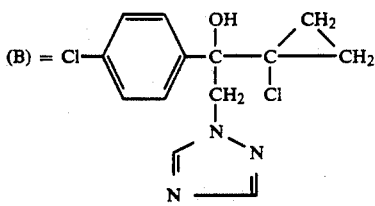

(disclosed in EP-OS (European Published Specification 0,180,136)

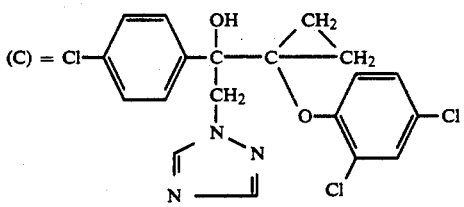

(disclosed in EP-OS (European Published Specification) 0,180,136)

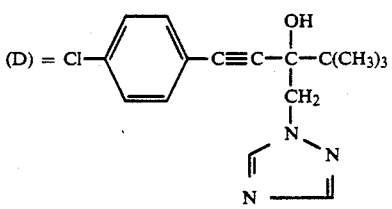

(disclosed in EP-OS (European Published Specification) 0,052,424)

Example A

Erysiphe test (wheat)/protective

Solvent: 100 parts by weight of dimethylformamide

Emulsifier: 0.25 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. tritici.

The plants are placed in a greenhouse at a temperature of about 20° C. and a relative atmospheric humidity of about 80%, in order to promote the development of powdery mildew pustules.

Evaluation is carried out 7 days after the inoculation.

In this test, the compounds (V-1), (V-2), (V-3) and (V-4) show a considerably better activity than the comparison substances (B) and (C).

Example B

Puccinia test (wheat) / protective

Solvent: 100 parts by weight of dimethylformamide

Emulsifier: 0.025 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of Puccinia recondita within a 0.1% strength aqueous agar solution. After the spore suspension has dried on, the plants are sprayed with the preparation of active compound until dew-moist. The plants remain in an incubation cabin at 20° C. and 100% relative atmospheric humidity for 24 hours.

The plants are placed in a greenhouse at a temperature of about 20° C. and a relative atmospheric humidity of about 80%, in order to promote the development of rust pustules.

Evaluation is carried out 10 days after the inoculation.

In this test, the compounds (V-1), (V-2), (V-3), (V-4) and (V-5) show a considerably better activity than the comparison substance (A).

Example C

Venturia test (apple)/protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaqualis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, the compounds (V-1), (V-2) and (V-5) show a considerably better activity than the comparison substance (C).

Example D

Erysiphe test (barley)/protective

Solvent: 100 parts by weight of dimethylformamide

Emulsifier: 0.25 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, the compound (XVII-1) shows a considerably better action than the comparison substance (D).

Example E

Uromyces test (dwarf bean)/protective
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous uredospore suspension of the bean rust causative organism (*Uromyces appendiculatus*) and remain in a dark humidity chamber at 20° to 22° C. and 100% relative atmospheric humidity for 1 day.

The plants are then placed in a greenhouse under intensive illumination at 20° to 22° C. and a relative atmospheric humidity of 70 to 80% for 9 days.

Evaluation is carried out 10 days after the inoculation.

In this test, the compound (XVII-1) shows a better activity than the comparison substance (D).

Example F

Pyricularia test (rice)/protective
Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous sport suspension of *Pyricularia oryzae*. The plants are then placed in a greenhouse at 100% relative atmospheric humidity and 25° C.

Evaluation of the disease infestation is carried out 4 days after the inoculation.

In this test, the compound (XVII-1) shows a considerably better activity than the comparison substance (D).

It will be appreciated that the instant specification and claims are set forth by way of illustration and not limitation, and that various modifications and changes may be made without departing from the spirit and scope of the present invention.

What is claimed is:

1. A 2,2-difluorocyclopropyl derivative of the formula

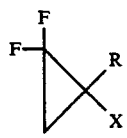

in which
R represents alkyl having 1 to 4 carbon atoms, phenyl or benzyl and
X represents hydroxymethyl or 2-hydroxyethyl.

2. A 2,2-difluorocyclopropyl derivative according to claim 1, in which
represents methyl, ethyl, isopropyl, tert.-butyl phenyl.

3. A 2,2-difluorocyclopropyl derivative according to claim 1, in which said compound is 2-(2,2-difluoro-1-methylcyclopropyl)-ethanol of the formula

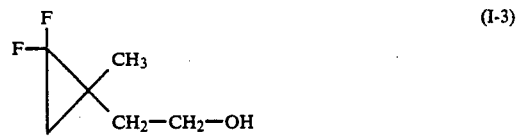
(I-3)

4. A 2,2-difluorocyclopropyl derivative according to claim 1, in which said compound is 2,2-difluoro-1-methylcyclopropyl-methanol of the formula

(I-5)

* * * * *

UNITED STATES PATENT AND TRADEMARK OFFICE
CERTIFICATE OF CORRECTION

PATENT NO. : 5,208,388
DATED     : May 4, 1993
INVENTOR(S) : Gassen, et al.

It is certified that error appears in the above-identified patent and that said Letters Patent is hereby corrected as shown below:

Col. 30, line 26    Before " represents " insert -- R --

Col. 30, line 27    After " phenyl " insert -- or benzyl --

Signed and Sealed this

Sixteenth Day of August, 1994

Attest:

BRUCE LEHMAN

*Attesting Officer*      *Commissioner of Patents and Trademarks*